(12) United States Patent
Rubery et al.

(10) Patent No.: US 7,704,272 B2
(45) Date of Patent: *Apr. 27, 2010

(54) METHOD FOR INTRODUCING AN ULTRAVIOLET LIGHT ACTIVATED VIRAL VECTOR INTO THE SPINAL COLUMN

(75) Inventors: Paul T. Rubery, Honeoye Falls, NY (US); Edward M. Schwarz, Rochester, NY (US)

(73) Assignee: University of Rochester, Rochester, NY (US)

(*) Notice: Subject to any disclaimer, the term of this patent is extended or adjusted under 35 U.S.C. 154(b) by 18 days.

This patent is subject to a terminal disclaimer.

(21) Appl. No.: 10/357,273

(22) Filed: Jan. 31, 2003

(65) Prior Publication Data

US 2004/0049249 A1 Mar. 11, 2004

Related U.S. Application Data

(60) Provisional application No. 60/353,907, filed on Jan. 31, 2002.

(51) Int. Cl.
*A61N 5/06* (2006.01)
*A01N 63/00* (2006.01)

(52) U.S. Cl. .................. 607/88; 607/89; 424/93.1; 424/93.2; 424/93.21

(58) Field of Classification Search ......... 435/455–469, 435/448, 488; 606/1, 3, 10–19; 607/2, 3–19; 424/93.1, 93.2, 93.21
See application file for complete search history.

(56) References Cited

U.S. PATENT DOCUMENTS

| | | |
|---|---|---|
| 4,671,273 A | 6/1987 | Lindsey |
| 4,846,172 A | 7/1989 | Berlin |
| 5,084,043 A * | 1/1992 | Hertzmann et al. ............ 606/3 |
| 5,188,632 A | 2/1993 | Goldenberg |
| 5,201,729 A | 4/1993 | Hertzmann et al. |
| 5,242,439 A | 9/1993 | Larsen et al. |

(Continued)

FOREIGN PATENT DOCUMENTS

DE 34 15 293 A1 11/1985

(Continued)

OTHER PUBLICATIONS

Ariizumi et al; "Wavelength-specific induction of immediate early genes by ultraviolet radiation"; J. Derm. Sci.; 12; 1996; pp. 147-155.*

(Continued)

*Primary Examiner*—David Shay
(74) *Attorney, Agent, or Firm*—Knobbe Martens Olson & Bear LLP

(57) ABSTRACT

In accordance with the present invention, methods and structures are provided for the treatment of functional spinal unit injuries through the use of light activated gene therapy to induce bone fusion through the introduction of a desired gene into a patient's spinal tissue. Methods and structures are also provided for the utilization of ultraviolet light activated gene therapy to repair/rebuild an injured intervertebral disc through the introduction of a desired gene into a patient's spinal tissue. An implant system including a light probe and an implant with which r-AAV is integrated is also provided.

32 Claims, 8 Drawing Sheets

U.S. PATENT DOCUMENTS

| | | | |
|---|---|---|---|
| 5,340,734 | A | 8/1994 | Della-Cioppa et al. |
| 5,604,090 | A | 2/1997 | Alexander et al. |
| 5,834,182 | A | 11/1998 | Alexander et al. |
| 5,843,459 | A | 12/1998 | Wang et al. |
| 6,149,896 | A | 11/2000 | Riklis et al. |
| 6,254,547 | B1 * | 7/2001 | Phillips ................. 600/532 |
| 6,521,750 | B2 * | 2/2003 | Hair et al. ............... 530/350 |
| 6,593,084 | B2 * | 7/2003 | Bird et al. .................. 435/6 |
| 6,632,002 | B1 * | 10/2003 | Chubb et al. ............ 362/228 |
| 6,900,197 | B2 * | 5/2005 | Szabo et al. ............. 540/145 |
| 7,524,327 | B2 | 4/2009 | Schwarz et al. |
| 2002/0168388 | A1 | 11/2002 | Borchert |
| 2003/0023284 | A1 | 1/2003 | Gartstein et al. |
| 2003/0175959 | A1 | 9/2003 | Fusenig |
| 2003/0236394 | A1 | 12/2003 | Schwarz et al. |
| 2004/0264853 | A1 | 12/2004 | Schwarz et al. |
| 2005/0055072 | A1 | 3/2005 | Rubery et al. |
| 2009/0093867 | A1 | 4/2009 | Schwarz et al. |

FOREIGN PATENT DOCUMENTS

| | | |
|---|---|---|
| DE | 42 19 626 A1 | 12/1993 |
| DE | 43 36 989 A1 | 5/1995 |
| DE | 29716011 U | 10/1997 |
| EP | 0 152 686 A1 | 8/1985 |
| EP | 0 680 517 B2 | 1/2005 |
| WO | WO 89/03202 A2 | 4/1989 |
| WO | WO 99/47177 | 9/1999 |
| WO | WO 2004/069326 A | 8/2004 |

OTHER PUBLICATIONS

Peak et al "DNA-to-Protien Crosslinks and Backbone Breaks Caused by Far- and Near-Ultraviolet and Visible Light radiations in Mammalian Cells"; Basic Life Sciences; vol. 38; 1986; pp. 193-202.*
Koeberl, et al., "Persistent expression of human clotting factor IX from mouse liver after intravenous injection of adeno-associated virus vectors," *Proc. Natl. Acad. Sci. USA*, vol. 94, pp. 1426-1431 (1997).
Yang, et al., "Adeno-associated virus vector mediated transduction of primary normal human breast epithelial cells," *Oncology Reports*; 5:793-797 (1998).
Edward M. Schwarz, Ph.D., *The Adeno-Associated Virus Vector for Orthopaedic Gene Therapy*, Clinical Orthopaedics and Related Research, No. 379S, pp. S31-S39.
Goater et al. *Empirical Advantages of Adeno Associated Viral Vectors for in Vivo Gene Therapy for Arthritis*, J Rheumatol, 2000; vol. 27: pp. 983-989.
Alexander et al. *Effects of Gamma Irradiation on the Transduction of Dividing and Nondividing Cells in Brain and Muscle of Rats by Adeno-Associated Virus Vectors*, Human Gene Therapy, vol. 7; May 1, 1996: pp. 841-850.
Russell et al., *DNA synthesis and topoisomerase inhibitors increase transduction by adeno-associated virus vectors*, Proc. Natl. Acad. Scil USA; vol. 92, Jun. 1995: pp. 5719-5723.
Russell et al., *Adeno-associated virus vectors preferentially transduce cells in S phase*, Proc. Natl. Acad. Sci. USA; vol. 91, Sep. 1994: pp. 8915-8919.
Alexander et al., *DNA-Damaging Agents Greatly Increase the Transduction of Nondividing Cells by Adeno-Associated Virus Vectors, Journal of Virology*, Dec. 1994: pp. 8282-8287.
Alford et al. "Cartilage Restoration, Part 1" American Journal of Sports Medicine (2005), 33(2):295-306.
Evans et al. "Osteoarthritis gene therapy" Gene Therapy (2004) 11:379-389.
Goater et al. "Empirical Advantages of Adeno-Associated Viral Vectors for in Vivo Gene Therapy for Arthritis" University of Rochester Medical Center, pp. 1-24.
Ito et al. "Light-activated gene transduction of recombinant adeno-associated virus in human mesenchymal stem cells" Gene Therapy (2004) 11:34-41.
Madry et al. "Recombinant Adeno-Associated Virus Vectors Efficiently and Persistently Transduce Chondrocytes in Normal and Osteoarthritic Human Articular Cartilage." Human Gene Therapy (2003) 14:393-402.
Pan et al. "Disease-Inducible Transgene Expression from a Recombinant Adeno-Associated Virus Vector in a Rat Arthritis Model." Journal of Virology (1999) pp. 3410-3417.
Trippel et al. "Gene-based approaches for the repair of articular cartilage." Gene Therapy (2004) 11:251-359.
Ulrich-Vinther et al. "Light-Activated Gene Transduction Enhances Adeno-Associated Virus Vector-Mediated Gene Expression in Human Articular Chondrocytes." Arthritis & Rheumatism (2002) 46(8): 2095-2104.
Yang et al. "ATM, ATR and DNA-PK: initiators of the cellular genotoxic stress responses." Carcinogenis (2003) 24(10)1571-1580.
Zhang et al. "Requirement of ATM in UVA-induced Signaling and Apoptosis." J Biological Chem (2002) 277(5): 3124-3131.
Alberts et al, *Molecular Biology of the Cell*, $4^{th}$ ed, 2002, pp. 267-269.
Glen Research Glen Report, "Thymine Dimers—DNA Lesions Induced by Sunlight CIS-SYN Thymine Dimer Phosphoramidite Now Available" Dec. 17, 2003; accessed Oct. 27, 2005 from http://glenres.com/GlenReports/GR16-21.html, 2 pages.
Kornberg et al, DNA Replication, $2^{nd}$ Ed, 1992, p. 772.
Maloney et al. Safety and efficacy of long wavelength ultraviolet light-activated gene transduction for site-specific gene therapy of articular cartilage defects. In review. 34 pages.
Stryer, *Biochemistry*, $2^{nd}$ ed., 1981, pp. 587-588.
Vink et al. Biological consequences of cyclobutane pyrimidine dimmers. J Photochem & Photobiol B Biol, 2001, 65:101-104.
Zubay, *Biochemistry*, 1983, pp. 768-771.
Summary Statement, 9 pages.
Nakai et al. "Extrachromosomal Rembinant Adeno-Associated Virus Vector Genomes Are Primarily Responsible for Stable Liver Transduction In Vivo," Journal of Virology, Aug. 2001, p. 6969-6976.
Nakai et al. "Unrestricted Hepatocyte Transduction with Adeno-Associated Virus Cerotype 8 Vectors in Mice." Journal of Virology, Jan. 2005, p. 214-224.
Jiang et al. "Effects of transient immunosuppression on adenoassociated, virus-mediated, liver-directed gene transfer in rhesus macacques and implications for human gene therapy." Blood (2006), 108:3321-3328.
Manno et al. "Successful transduction of liver in hemophilia by AAV-Factor IX and limitations imposed by the host immune response." Nature Medicine, Mar. 2006, 12(3): 342-347, 592.
Supplementary European Search Report, European Appl. No. 06 124 972.8-1223, dated Nov. 14, 2007, 8 pages.
Office Action dated Aug. 29, 2007, received in U.S. Appl. No. 10/769,392.
Han et al. "Induction of DNA-protein cross-linking in Chinese hamster cells by monochromatic 365 and 405 nm ultraviolet light" Photochemistry and Photobiology 1984, 39(3) 343-348.
Kulms et al. "Molecular mechanisms of UV-induced apoptosis" Photodermatol Photoimmunol Photomed 2000; 16:195-201.
Miyamoto et al. "Ultraviolet Cross-Linking of DNA Binding Proteins", Methods in Enzymology, 1995, vol. 254, p. 632-641.
Peak et al. "DNA-to-Protein Crosslinks and Backbone Breaks Caused by Far- and Near-Ultraviolet, and Visible Light Radiations in Mammalian Cells", Basic Life Sciences, 1986. vol. 38, p. 193-202.
Peak et al. "Induction of DNA-protein crosslinks in human cells by ultraviolet and visible radiations: action spectrum" Photochemistry and Photobiology, 1985, 41(3) 295-302.
Office Action dated Dec. 26, 2007, received in U.S. Appl. No. 10/357,271, 9 pages.
Office Action dated Feb. 14, 2008, received in U.S. Appl. No. 10/769,392, 9 pages.
Communication Pursuant to Art 96(2) EPC, received in European Appl. No. 04707090.9, dated Mar. 15 2007.
File History of U.S. Appl. No. 10/357,271, filed Jan. 31, 2003.
File History of U.S. Appl. No. 10/769,392, filed Jan. 30, 2004.
File History of U.S. Appl. No. 10/942,353, filed Sep. 15, 2004.
Extended European Search Report, European Appl. No. 08101769.1, dated May 28, 2008, 6 pages.

Office Action dated Jul. 9, 2008, received in U.S. Appl. No. 10/942,353.
Adeno-associated virus. Wikipedia entry dated Aug. 5, 2009. Accessed at http://en.wikipedia.org/wiki/Adeno-associated_virus.
Fauquet et al. Virus Taxonomy, International Committee on Taxonomy of Viruses, Elsevier Academic Press, 2005. p. 368.
Office Action dated Aug. 6, 2009, received in U.S. Appl. No. 10/942,353.
Advisory Action dated Jun. 22, 2009, received in U.S. Appl. No. 10/769,392.
Interview Summary dated May 14, 2009, received in U.S. Appl. No. 10/769,392.
File History of U.S. Appl. No. 12/203,056, filed Sep. 2, 2008.
Notice of Allowance dated Aug. 25, 2008, received in U.S. Appl. No. 10/357,271.
Office Action dated Feb. 23, 2009, received in U.S. Appl. No. 10/942,353.
Office Action dated Oct. 2, 2008, received in U.S. Appl. No. 10/769,392.
Office Action dated Mar. 18, 2009, received in U.S. Appl. No. 10/769,392.
Advisory Action dated May 4, 2009, received in U.S. Appl. No. 10/942,353.
Friedberg, "DNA damage and repair," Nature, Jan. 23, 2003, pp. 436-440, vol. 421, Nature Publishing Group.
Pandori M.W. et al. Photoactivatable retroviral vectors: A strategy for targeted gene delivery. *Gene Therapy* Dec. 2000, vol. 7 No. 23 p. 1999-2006.

* cited by examiner

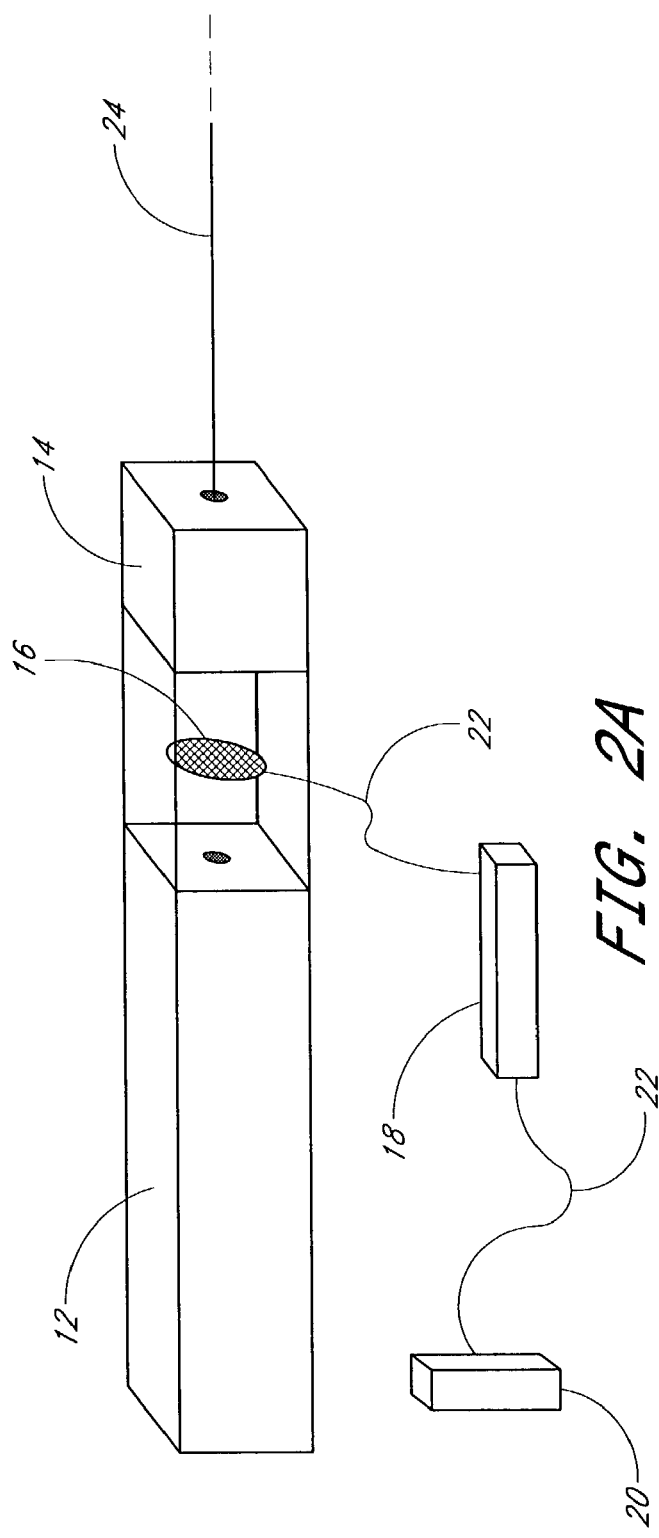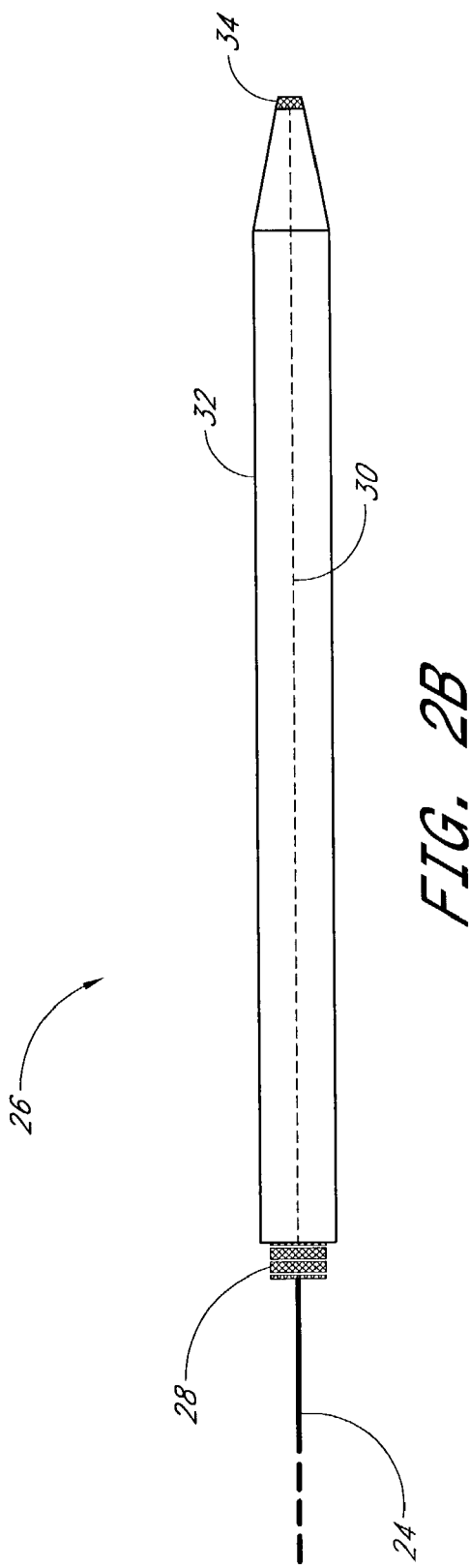
FIG. 2A
FIG. 2B

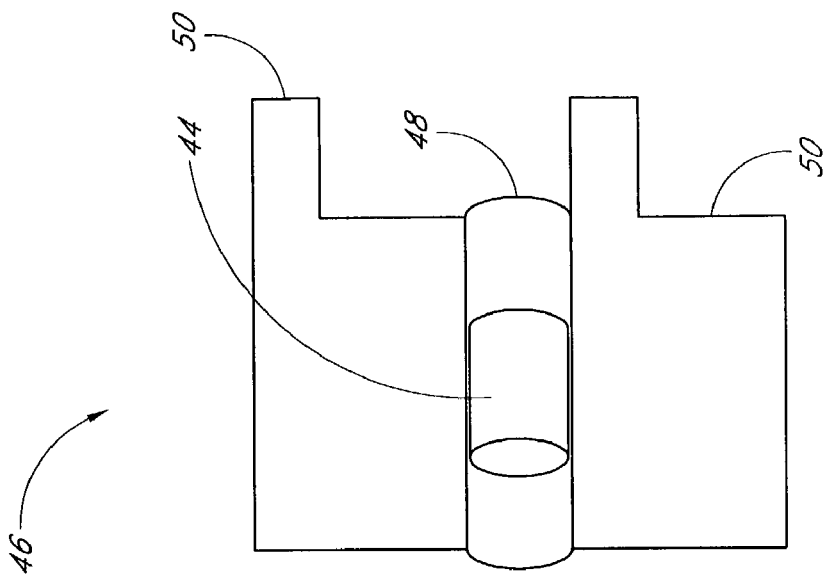
FIG. 4E
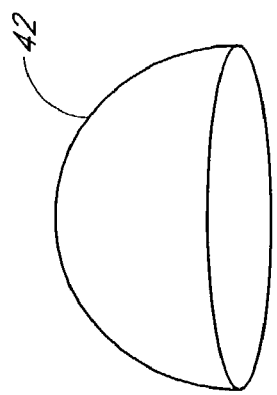
FIG. 4B
FIG. 4D
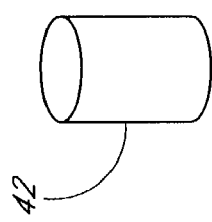
FIG. 4A
FIG. 4C

METHOD FOR INTRODUCING AN ULTRAVIOLET LIGHT ACTIVATED VIRAL VECTOR INTO THE SPINAL COLUMN

RERFERENCE TO RELATED APPLICATIONS

The present application claims the priority benefit under 35 U.S.C. §119(e) of Provisional Application No. 60/353,907, filed on Jan. 31, 2002. The present application is also related to Provisional Application No. 60/353,842, filed on Jan. 31, 2002, and U.S. application Ser. No. 10/357,271, filed on Jan. 31, 2003.

GOVERNMENT INTEREST

This invention was made with Government support under NIH Contract #AR45971, an RO1 grant awarded by NIAMS. The Government has certain rights in the invention.

BACKGROUND OF THE INVENTION

1. Field of the Invention

The present invention relates to the field of gene therapy. According to the present invention, methods are provided for the treatment of functional spinal unit injuries through the use of light activated gene therapy to introduce a desired gene into a patient's tissue. An embodiment of the present invention includes methods for the utilization of light activated gene therapy to repair/rebuild an injured intervertebral disc. Alternate embodiment provide an implant system having UV activated viral vector integrated with an implant.

2. Description of the Related Art

Currently, treatment for injured spines often involves "fusion" or inciting the biological union of bones by inserting bone grafts or devices within the functional spinal units (FSU), e.g., between two vertebra. In addition, the effective manipulation of certain osteobiologic molecules via gene therapy can be used to incite bone fusion within a functional spinal unit (FSU). A FSU is composed of two vertebra, a nearby nerve root, and a human interverterbral disc between the two vertebra. This disc, which cushions shock to the spine and lends stability to the FSU, is composed of water, collagen (Type I and II), and glycosaminoglycans (GAG).

An aging or degenerate disc is often characterized by reduced water, increased Type I collagen, decreased Type II collagen, and decreased GAG. This aging or degenerating, which is incompletely understood, generally results in decreased biomechanical shock absorption, increased range of motion and pain and/or disability.

Somatic cell gene therapy is a form of treatment in which the genetic material of a target cell is altered through the administration of nucleic acid, typically in the form of DNA. In pursuit of effective in vivo administration routes, scientists have harnessed the otherwise potentially deleterious ability of viruses to invade a target cell and "reprogram" the cell through the insertion of viral DNA. By encapsulating desirable genetic material in a viral particle, or "vector," minus some of the viral DNA, the effective and targeted delivery of genetic material in vivo is possible. As applied to spinal specific treatments, gene therapy offers the ability to make use of osteobiological molecules, including both intracellular and extracellular proteins, to incite bone fusion and/or disc repair.

In particular, the desirable qualities of adeno-associated viruses (AAV) have led to further study of potential gene therapy uses. As a vehicle for gene therapy recombinant forms of AAV, or r-AAV, offer many advantages including the vector's ability to infect non-dividing cells (e.g., chondrocytes, or cells within cartilage), the sustained target gene expression, the low immune response to the vector, and the ability to transduce a large variety of tissues. The AAV contains a single strand DNA (ssDNA) genome. Under normal conditions, AAV is present in humans in a replication incompetent form, due to the fact the AAV alone does not encode the enzyme required for replication of the second DNA strand. Successful r-AAV transduction often requires the presence of a co-infection with an adenovirus or the exposure of the host cell to DNA damaging agents, such as γ-irradiation. The introduction of either the co-infection or the DNA damaging agents dramatically induces the rate limiting step of second strand synthesis, i.e. the second strand of DNA which is synthesized based on the vector inserted first strand. However, making use of these DNA damaging agents is impractical because the administration of an adenovirus co-infection to a patient is not practical or desirable and the site specific and safety issues involved with using γ-irradiation are undesirable as well.

In the past, attempts have been made to induce r-AAV transduction in vitro using UV radiation having a wavelength of 254 nm. Unfortunately, no effective therapeutic method or apparatus was developed based on these experiments due to the long exposure times involved with using 254 nm UV radiation, the difficulties of delivering 254 nm UV radiation to a surgical target site, and the inability to position the 254 nm UV light source so as to allow effective penetration of a target cell.

SUMMARY OF THE INVENTION

Preferred embodiments of the present invention provide structures and methods for treating a patient's spine using light activated gene therapy.

In accordance with an embodiment of the present invention, a method of introducing a desired gene into a patient's spinal tissue is provided. A light probe is locating proximate to target cells. The transduction of the ultraviolet light activated viral vector is activating by locally administering ultraviolet light to spinal target cells using the light probe. The ultraviolet light activated viral vector is delivered proximate to the spinal target cells.

In accordance with another embodiment of the present invention, a method of introducing a desired gene into a patient's spinal tissue is provided including inserting an implant proximate to spinal target cells within the patients spinal tissue. A light probe is located proximate to spinal target cells. The transduction of a ultraviolet light activated viral vector is activated by locally administering ultraviolet light to spinal target cells using the light probe. The ultraviolet light activated viral vector is delivered proximate to the spinal target cells.

In accordance with yet another embodiment of the present invention, a spinal implant system for introducing a desired gene into a patient's tissue is provided. The system includes an expandable implant configured to be inserted into a patient's spine in a minimally intrusive surgical procedure and an ultraviolet activated viral vector integrated with the expandable spacer.

In accordance with still another embodiment of the present invention, a gene therapy system for increasing the transduction of an ultraviolet light activated viral vector in a patient's spinal tissue is provided. The gene therapy system includes a power source which powers a light source producing an ultraviolet light beam. An optical coupler is also included for guiding the light beam into a light delivery cable. A timed shutter, having a user interface for controlling the shutter, is located in line with the light beam. A light probe, which receives the light beam from the light delivery cable, is configured to output the light beam proximate to the target cells in a patient's spine in order to increase the transduction of the ultraviolet light activated viral vector. An optical connector connects the light delivery cable to the light probe.

A feature of preferred embodiments of the present invention the ability to overcome the problems involved with using traditional UV and γ-irradiation, by using locally administered UV, preferably long wavelength UV light, in order to induce the target cells to more effectively stimulate the transduction of a UV activated viral vector, such as recombinant adeno-associated virus r-AAV. In certain preferred embodiments, the desirable genetic material carried in the UV activated viral vector is then able to facilitate the rebuilding of important components of the FSU, such as GAG and collagen, or to effect bone formation resulting in fusion.

BRIEF DESCRIPTION OF THE DRAWINGS

FIG. 2A is a side view schematic of the light source and user interface components of a light probe system, in accordance with another embodiment of the present invention.

FIG. 2B is a schematic of light probe forming part of the light probe system shown in FIG. 2A.

FIGS. 4A-D are perspective schematics of example collapsible spinal implants, in accordance with yet another embodiment of the present invention.

FIG. 4E is a cross section schematic of the expanded implant of FIG. 4D, the expanded implant shown located between two vertebra.

DETAILED DESCRIPTION OF THE PREFERRED EMBODIMENT

The term "AAV" refers to adeno-associated virus, while "r-AAV" refers to recombinant adeno-associated virus. Preferably, r-AAV includes only a gene, which is desired to be introduced into the patient's spinal tissue, and the flanking AAV inverted terminal repeats (ITR's) that serve as the packaging signals.

"Ultraviolet radiation" and "ultraviolet light," also known as "UV", refer to the portions of the electromagnetic spectrum which have wavelengths shorter than visible light. The range of wavelengths considered to be ultraviolet radiation, from about 4 nanometers to about 400 nanometers, is further subdivided into three subgroups, UVA, UVB, and UVC. "UVA" is the portion of ultraviolet radiation which includes wavelengths from 320 nm up to and including 400 nm. "UVB" is the portion of ultraviolet radiation which includes wavelengths from 280 nm up to and including 320 nm. "UVC" is the portion of ultraviolet radiation having a wavelength less than 280 nm.

The term "long wavelength UV" refers to ultraviolet radiation or light having a wavelength greater than or equal to 255 nm, but not more than 400 nm.

A "viral vector" refers to a virus, or recombinant thereof, capable of encapsulating desirable genetic material and transferring and integrating the desirable genetic material into a target cell, thus enabling the effective and targeted delivery of genetic material both ex vivo and in vivo. A "UV activated viral vector" or "UV light activated viral vector" is any virus, or recombinant thereof, whose replication is regulated by ultraviolet light. Recombinant adeno-associated virus (r-AAV) is included in the group of viruses labeled UV activated viral vectors.

The term "LAGT" refers to light activated gene transduction, while "LAGT probe" or "light probe" or "long UV wavelength light probe" refers to the medical device which delivers ultraviolet light to the target site and effectuates the transduction of the desired gene carried by the vector.

"Implant" or "spacer implant" is any structure designed to be inserted proximate to the spine for the purpose of aiding the treatment of the spinal target site where the implant is inserted.

Figure 1:
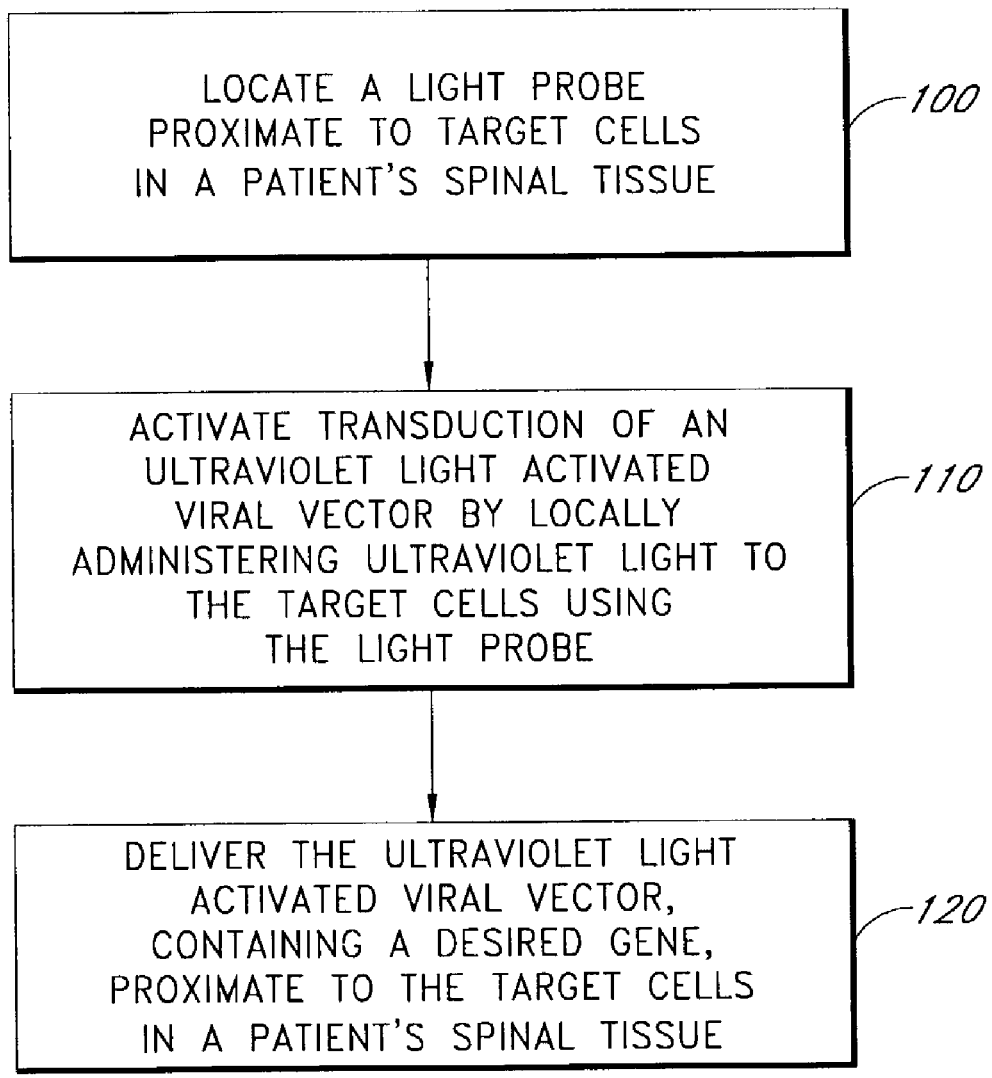
FIG. 1 is flowchart of a method of treating a patient's spinal tissue using a UV light activated viral vector and a UV light probe, in accordance with an embodiment of the present invention.

FIG. 1 shows a method of treating a patient's spinal tissue. A light probe is also located 100 proximate to target cells in a patient's spinal tissue. The transduction of an ultraviolet (UV) activated viral vector is then activated 110 by locally administering ultraviolet light to the target cells using the light probe. The ultraviolet (UV) activated viral vector, containing a desired gene, is delivered 120 proximate to the target cells.

It should be noted that the method of FIG. 1 may be performed in other preferred embodiments in a different order than the textually outlined above. For example, in another preferred embodiment the vector is delivered prior to locally administering the ultraviolet light.

In one preferred embodiment the LAGT probe activates a UV activated viral vector transduction, including r-AAV transduction, by radiating the viral vector infected target cell with locally administered UV radiation, while in a preferred alternate embodiment the target cell is activated with locally administered long wavelength UV radiation having a wavelength specifically from 255 nm up to and including 400 nm. In other preferred embodiments, the wavelength of the UV light ranges from about 280 to about 330. More preferably, the locally administered UW radiation has a wavelength from 315 nm to 355 nm, most preferably about 325 nm. In an alternate embodiment the ultraviolet radiation has a wavelength of about 4 nm to about 400 nm, while in another alternate embodiment the ultraviolet radiation has a wavelength of 290 nm.

FIGS. 2A and 2B illustrate separate components of a UV radiation delivery system, with FIG. 2A showing the UV light generator 10, user interface system, and FIG. 2B showing the light probe 26. Note the light probe 26 is operatively connected to the UV light generator 10 by the light delivery cable 24.

With reference to FIG. 2A, the UV radiation delivery system includes a light source 12 with the desired wavelength UV output. In addition, an optical coupler 14 transmits the light from the light source 12 into a light delivery cable 24, such as an optical fiber cable or bundle, that transmits the light to the target site via a light probe 26 (FIG. 2B). A timed shutter 16 is located in the path of the light beam between the light source 12 and the optical coupler 14 in order to control the length of time the patient is exposed to UV light via the light probe 26 (FIG. 2B). The timed shutter 16 is operatively connected via connectors 22 to a shutter controller 18 and a shutter control interface 20.

FIG. 2B shows a light probe 26 as a component of UV radiation delivery system for use with the component, shown in FIG. 2. The light probe 26 is configured to locally irradiate a target cells infected by a UV activated viral vector. The light probe 26 fiber-optically transmit an appropriate wavelength light, which originates from the light source 12 (FIG. 2A), through a light guide 30 to a light guide terminator 34 configured to irradiate target cells with UV light and thereby "activate" r-AAV transduction in the target cells. The light guide 30 is preferably surrounded by a housing 32. The light guide terminator 34, e.g., a microlens or cylindrical diffusing lens, is preferably configured to allow the effective irradiation of the desired target cells. The light probe 26 is preferably both shaped in the form of an arthroscope and interchangeable with alternate light probes having a differing configurations. For example, the light probe can be configured to have different forms in order to more effectively access different treatment sites. Preferably, the optical connector 28 also allows the light probe 26 to be selectively detached from the light delivery cable 24 when desired. The light probe 26 is also preferably configured to be sterile and disposable. In certain alternate embodiments, the UV radiation delivery system also includes a targeting laser beam to enable accurate delivery of the light. Standard surgery tools as recognized by those skilled in the art, for example cannulas and trochars, may also be incorporated into the disclosed method.

In the embodiment shown in FIG. 2A, the light source is contained within a housing, while in certain alternate embodiments the light source is operatively joined to the housing. It should be understood that the exact shape and size of the light probe 26 shown in FIG. 2A, and especially the light probe tip, will vary depending on the particular application and target site as would be understood by one skilled in the art. For example, the light probe 26 can be configured to access an intervertebral disc in a patient's spine or the cartilage in a patient's joint. The preferred embodiments include a light source comprising a laser tuned to the appropriate long UV wavelength. In preferred embodiments, the UV radiation delivery system, whether it be a lamp or laser based system, will be optimized based on considerations such as cost and technical simplicity. In addition, the UV radiation delivery system can also include a targeting laser beam to enable accurate delivery of the light. Standard surgery tools, for example cannulas and trochars, may also be used. In accordance with alternate embodiments, the light probe could be designed for external use, such as irradiating an implant having r-AAV integrated therewith, outside of the patient and subsequently inserting the implant to a spinal target site.

Alternate embodiments of the UV radiation delivery system employ as a light source, a lamp, such as a high intensity argon lamp. In these alternate embodiments, the UV radiation delivery system further includes a wavelength selecting device, such as a dichroic mirror and/or optical filter, set to transmit the desired wavelength UV light and reject unwanted light wavelengths.

Figure 3:
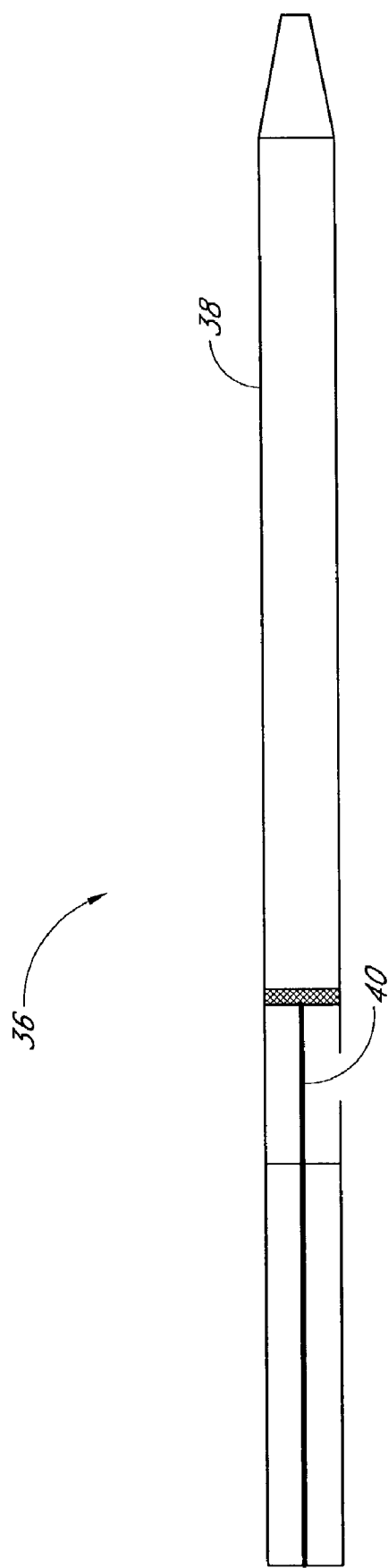
FIG. 3 is a schematic of a syringe for introducing a UV activated vector into a patient's spinal tissue.

As shown in FIG. 3, an injecting device 36 having a housing 38 and a plunger mechanism 40 is preferably employed in conjunction with the UV radiation delivery system of FIGS. 2A and 2B. Preferably, the injecting device 36 is configured for delivering a UV activated viral vector, such as r-AAV, to the target site using minimally invasive surgical techniques. In alternate preferred embodiments, the injecting device can be configured to inject an implant to a target site in a patient.

Surgery tools, other than the injecting device 36 shown in FIG. 3, which can be involved in certain preferred embodiments include a cannula, a trochar and a power percutaneous disc resector, (all not shown) which increases space within a disc space. It should be noted that the size and design of these tools would vary to adapt to both the treatment goal and the target site. Alternate embodiments of these tools would be designed to access cervical, thoracic, and lumbar disk spaces, as well as the facet joints.

Referring to FIGS. 4A-4E, alternate preferred embodiments provide a spinal implant system, including "spacer" implants which create temporary mechanical rigidity between discs while the target cells respond to the introduction of the desired gene into the patient's tissue. These solid platforms are preferably expandable and designed as surgical implants. These carefully engineered solid platforms or implants can also be formed in a number of shapes, including but not limited to an unfolding geodosic dome 42 or tetrahedrons (not shown), umbrella/dome (not shown), an expanding cylinder 44, and springs which uncoil to increase diameter. Expanding cylinder 44 is shown in a compacted shape in FIG. 4A and an expanded state in FIG. 4B (and also FIG. 4E), while unfolding geodosic dome 42 is shown in a compacted shape in FIG. 4C and an expanded state in FIG. 4D. Preferably, these implants are produced with implant integrated UV activated viral vector. For example, r-AAV can be integrated with the implant through bonding or coating the r-AAV to the implant, absorbing the r-AAV into the implant, and/or baking the r-AAV to the implant surface. In alternate preferred embodiments the implant is delivered to a target site separate from the UV activated viral vector. Non-limiting examples of solid platforms with which UV activated viral vectors could be integrated include spinal spacers, as shown in FIG. 6E, and also other spinal surgical implants.

FIG. 4E shows the expanding cylinder 44 of FIGS. 4A and 4B in an expanded state, to which a UV activated viral vector is preferably integrated, placed between two vertebra 50 in order to facilitate the rebuilding or repair of the intervertebral disc 48. In another embodiments the implant is delivered to a target site separate from the UV activated viral vector.

It should be understood that structural support implants incorporating such conventional structures as, for example, but not limited to, plates, rods, wire, cables, hooks, screws, are also advantageously useful with preferred embodiments provided herein. The support structure may be formed from material such as, but not limited to, metal, carbon-fiber, plastic, and/or reabsorbable material.

Figure 5:
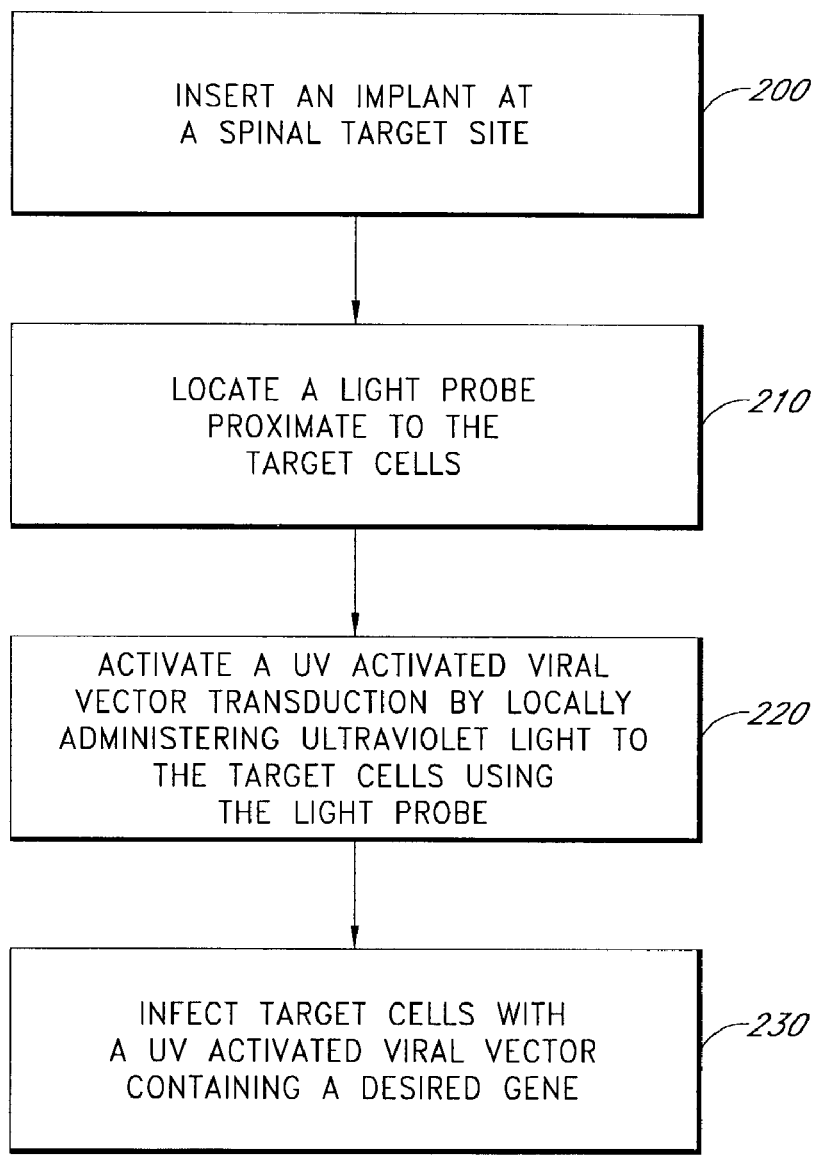
FIG. 5 is flowchart of a method of treating a patient's spinal tissue including a spinal implant, in accordance with a further embodiment of the present invention.

In another preferred embodiment, shown in FIG. 5, a implant is inserted 200 at a spinal target site, preferably using a minimally invasive route such as a stab incision. Target cells are infected 210 with a UV activated viral vector, such as r-AAV, containing a desired gene, preferably by attaching the vector to the implant prior to insertion. For example, r-AAV can be integrated with the implant through coating or bonding the r-AAV to the implant, absorbing the r-AAV into the implant, and/or baking the r-AAV to the implant surface. A light probe is placed or located 220 proximate to the target cells. The light probe activates 230 the infected target cell's UV activated viral vector transduction. In an alternative embodiment, the vector is delivered to the target site in a step separate from the insertion of the implant.

It should be noted that the method of FIG. 5, and the other methods provided herein, may depending on the desired order and outcome, be performed in other preferred embodiments in a different order than the textually outlined herein.

In certain preferred embodiments, the spacer implants can be used to reconstitute disk height and preserve FSU geometry while the surrounding bone fusion progresses. In these embodiments, the UV activated viral vector includes bone forming genes. The light probe would then directly activate target cells to transduct the viral vector.

In other embodiments employing spinal implants, the spacer implants can be used to reconstitute disk height and preserve FSU geometry while the invertebral disc regenerates to form a repaired or rejuvenated invertebral disc. In another preferred embodiment, structural support implants can be used to reconstitute disk height and preserve FSU geometry while the invertebral disc regenerates to form a repaired or rejuvenated invertebral disc. In these embodiments, the UV activated viral vector includes disc regenerating genes. In certain preferred embodiments, these structural support implants would be attached to bone, e.g., a plate screwed into the spinal column. The light probe would then directly activate target cells to transduct the viral vector.

In one embodiment the LAGT probe can activate the r-AAV transduction by irradiating the target cell with UV radiation, while in an alternate embodiment the target cell is activated with long wavelength UV radiation. Preferably, the injected r-AAV can carry bone forming genes and/or disc regenerating genes depending on the desired treatment goal. In addition, a spacer implant, in combination with bone forming genes, may be inserted between two vertebra in order to facilitate reconstituted disc height and bone fusion.

Embodiments of the present invention include both in vivo and ex vivo applications. In the ex vivo application the radiation dose would be applied to cells or biological material external to the patient and then delivered, preferably through injection, to the desired site of treatment. In the in vivo application the LAGT probe and the UV activated viral vector are preferably introduced to the treatment site using minimally invasive surgical techniques, such as stab incisions. Alternate in vivo embodiments employ direct visualization surgical techniques.

A UV light activated viral vector or UV activated vector is any virus, or recombinant thereof, whose replication is regulated by ultraviolet light. Preferred embodiments of UV activated viral vectors are viruses with single stranded DNA, the virus being capable of allowing a therapeutically significant increase in virus transduction when a virus infected target cell is exposed to a therapeutic dose of ultraviolet radiation. More preferred embodiments include UV activated viral vectors capable of infecting non-dividing cells, effectuating sustained target gene expression, eliciting a low immune response to the vector, and possessing an ability to transduce a large variety of tissues. Most preferably, the UV light activated vector is r-AAV.

Proof of principle experiments, both ex vivo and in vivo based, are currently under way to determine the optimal wavelengths for activating the gene therapy. The determination of more preferred wavelengths is based on among other factors, the ability to effectively penetrate a target cell, ease and efficiency of fiber optic transmission, the ability to trigger the transduction of a UV activated vector (such as r-AAV), and the length of time a patient must be exposed to receive a therapeutic dose of ultraviolet radiation. Preferably, the LAGT system delivers long wavelength ultraviolet radiation in the range of 315 nm to 400 nm. Current experiments support the use of ultraviolet radiation having a wavelength from 315 nm to 355 nm, but it is believed that these experiments will ultimately support ultraviolet radiation having a wavelength from 315 to 400 nm. In addition, alternate embodiments employ a laser which produces ultraviolet radiation having a wavelength of about 290 nm. Once specific wavelengths are determined, the disclosed components can be optimized for these specific wavelengths.

The wavelength of the ultraviolet light generated in order to activate UV activated viral vector transduction, including r-AAV transduction, in target cells is preferably 255, 256, 258, 265, 275, 285, 290, 295, 305, 314, 325, 335, 345, 355, 365, 375, 385, 395, or 400 nanometers. More preferably, the wavelength of the ultraviolet light is 290, 295, 300, 305, 310, 315, 316, 317, 322, 325, 327, 332, 337, 342, 347, 352, 357, 362, 367, 372, 377, 382, 387, 392, 393, 394, 395, 396, 397, 398, or 399 nanometers. Most preferably, the wavelength of the ultraviolet light is about 325 nanometers.

Table 1 shows example growth factors, signaling molecules and transcription factors which genes inserted into a viral vector could encode for in the practice of osico-integration and spine fusion. In certain preferred embodiments, genes encoding these molecules and factors are integrated with implants. The list contained in Table 1 is provided for illustrative purposes and should not be taken as limiting the embodiments of the invention in any way.

Table 2 shows example molecules which genes inserted into a viral vector could encode for in the practice of periprosthetic osteolysis. In certain preferred embodiments, genes encoding these molecules are integrated with implants. The list contained in Table 2 is provided for illustrative purposes and should not be taken as limiting the embodiments of the invention in any way.

TABLE 1 osteo-integration and spine fusion:

(a) GROWTH FACTORS

Transforming Growth Factor beta (TGFb) 1, 2 and 3
bone morphogenetic protein (BMP) 1, 2, 4, 6 and 7
parathyroid hormone (PTH) parathyroid hormone related peptide (PTHrP)
fibroblast growth factor (FGF) 1, 2
insulin-like growth factor (IGF)

(b) SIGNALING MOLECULES AND TRANSCRIPTION FACTORS

LMP-1
Smad 1, 5, 8 dominant-negative Smad 2, 3
Smurf2
Sox-9
CBFA-1
ATF2

TABLE 2 perioprosthetic osteolysis:

soluble tumor necrosis factor receptors TNFR, TNFR:Fc
osteoprotegerin (OPG)
interleukin-1 receptor antagonist (IL-1RA), IL-1RII:Fc
interleukin-4, 10 and viral IL-10

The results of a completed proof of principle experiment are shown in Example 1.

EXAMPLE 1

I. Methods

A. Isolation of Human Mesenchymal Stem Cells

Human Mesenchymal Stem Cells (hMSC) were isolated from patient blood samples harvested from the iliac crest. The blood samples were diluted in an equal volume of sterile Phosphate Buffered Saline (PBS). The diluted sample was then gently layered over 10 ml of Lymphoprep (Media Prep)

in a 50 ml conical tube (Corning). The samples were then centrifuged at 1800 rpm for 30 minutes. This isolation protocol is a standard laboratory technique, and the resulting gradient that formed enabled the isolation of the hMSCs from the layer immediately above the Lymphoprep. The isolated fraction was placed into a new 50 ml conical tube, along with an additional 20 ml of sterile PBS. The sample was centrifuged at 1400 rpm for 8 minutes. The supernatant was removed the cell pellet was resuspended in 20 ml for fresh PBS, and centrifuged again for 8 minutes at 1400 rpm. Afterwards the supernatant was removed, the cell pellet was resuspended in 10 ml of Dulbecco's Modified Eagle Medium (DMEM) with 10% Fetal Bovine Serum (FBS) and 1% Penicillin/Streptomycin (P/S) (Invitrogen). The hMSCs were grown and passed as necessary in a 37°/5% $CO_2$, water-jacketed incubator (Forma Scientific).

B. 325 nm UV treatment of Human Mesenchymal Stem Cells

Prior to irradiation, hMSCs were plated at a density of $5\times10^4$ cells/well in 12-well plates. The cells were allowed to sit down overnight. The next morning the media was removed immediately prior to irradiation. The cells were irradiated at various doses (500 $J/m^2$, 1000 $J/m^2$, 3000 $J/m^2$, 6,000 $J/m^2$, or 10,000 $J/m^2$) of 325 nm UV light using a helium-cadmium laser system (Melles Griot). After irradiation, fresh media, either with or without recombinant adeno-associated virus was added to the wells.

C. Infection of Human Mesenchymal Stem Cells with Recombinant Adeno-Associated Virus Infections were carried out in 12-well dishes. The cells were infected at various multiplicities of infection (MOIs=10, 100, and 1000), using a recombinant adeno-associated virus carrying the bacterial P-galactosidase reporter gene (rAAV-LacZ via UNC-Chapel Hill Gene Therapy Vector Core Facility). After being irradiated, the cells were infected with the predetermined amount of virus in a total volume of 500 μl of DMEM/10% FBS/1% P/S. Two hours after the initial infection, and additional 1 ml of media was added to the cultures. The cultures were then allowed to incubate (37°/5% $CO_2$) for forty-eight hours before harvest for analysis.

D. Quantifying Recombinant Gene Expression

Forty-eight hours after infection, the cells were harvested; cell lysates were made and analyzed using a commercially available Luminescent β-gal Reporter System. (BD Biosciences), Briefly, experimental cell samples were removed from the 12-well dish using 0.25% Trypsin-EDTA. The cell suspension was transferred to a 1.5 ml conical tube and the cells were pelleted via a 15 second centrifugation at 13,000 rpm. The cell pellet was washed using two successive rounds of resuspension in ice cold PBS and pelleting for 15 seconds at 13,000 rpm. The final pellet was resuspended in 75 μl of Lysis Buffer (100 mM $K_2HPO_4$, 100 mM $KH_2PO_4$, 1 M DTT) and subjected to three rounds of freeze/thaw in an isopropanol dry ice bath and a 37° water bath. The lysates were centrifuged for a final time for 5 minutes at 13,000 rpm. Aliquots (15 μl) of the resulting supernatant were incubated with the provided substrate/buffer solution for one hour and then analyzed using a standard tube luminometer. The read out of this analysis is expressed in Relative Light Units (RLU) in the Results section.

II. Results

A. Exposure to 325 nm UV Increased the Level of Reporter Gene Expression

Figure 6:
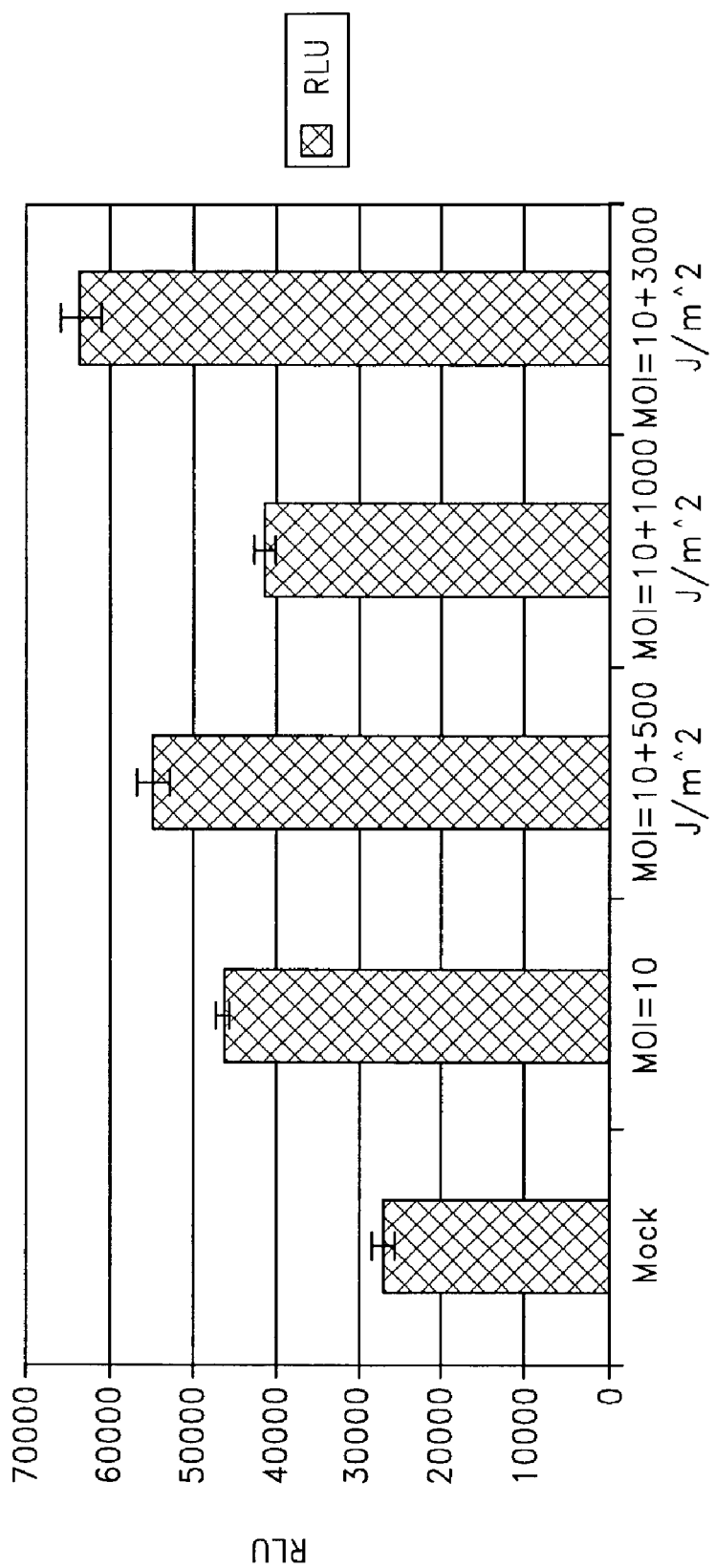
FIGS. 6-8 are graphs of the results of the proof of principle experiment of Example 1.
Figure 7:
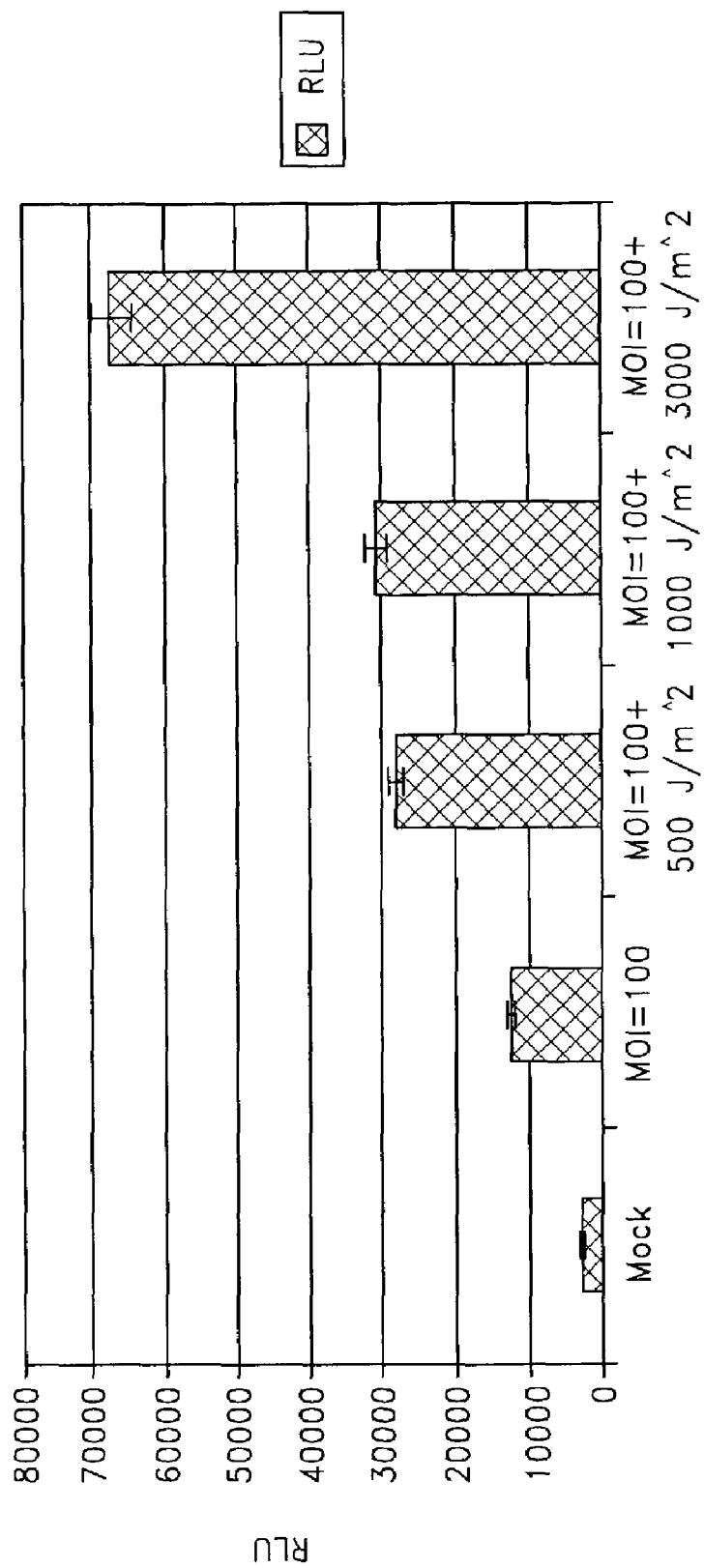
Figure 8:
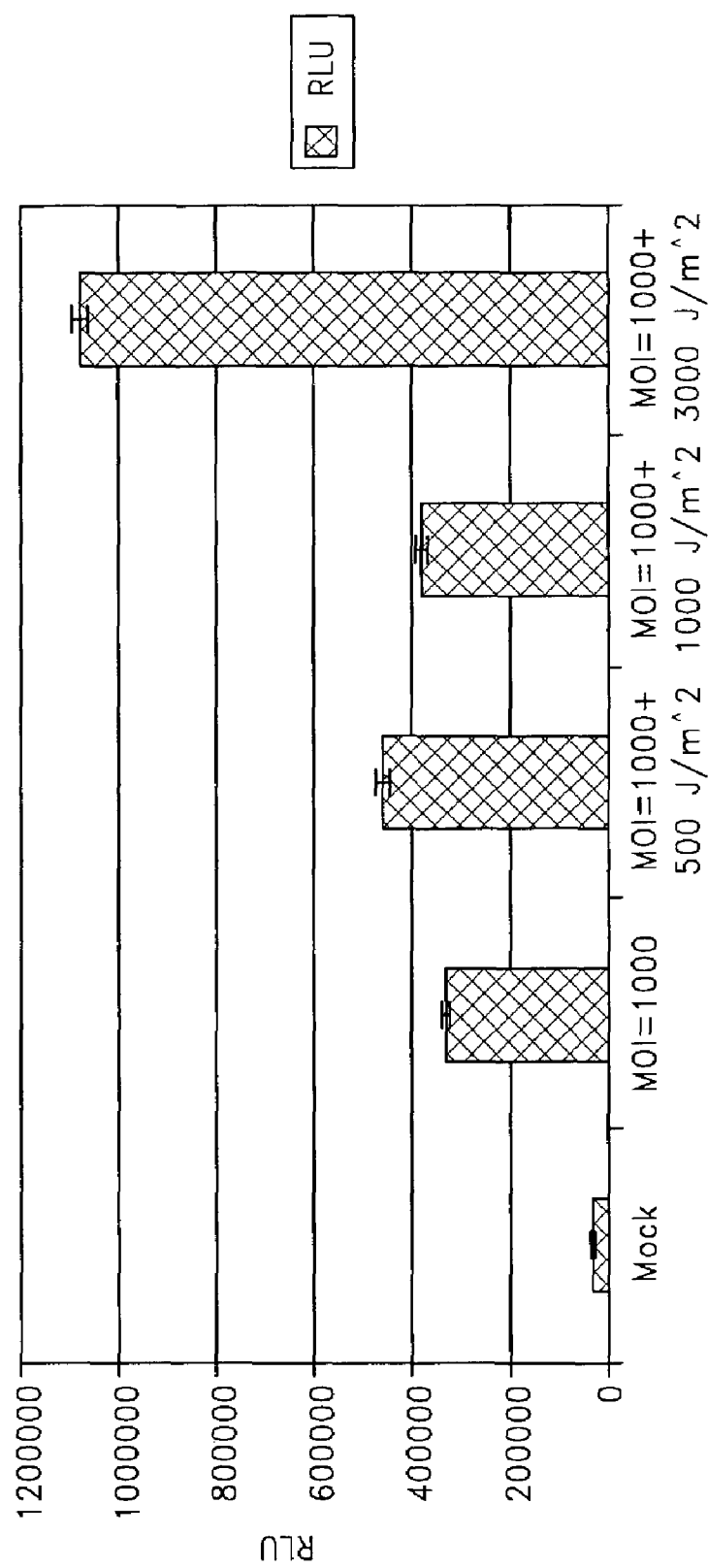

Exposure to 325 nm UV prior to infection with rAAV-LacZ had a dose dependent increase in LacZ reporter gene expression at each of the MOI's used. The controls for each experiment were as follows: Mock (cells alone, no treatment) and cells treated with each of the various UV dosages (500 $J/m^2$, 1000 $J/m^2$, 3000 $J/m^2$, 6000 $J/m^2$, which had RLU levels consistent with the Mock cultures (data not shown). Statistical significance was calculated using the Student T-Test. The results are shown in FIGS. 6-8.

Although this invention has been disclosed in the context of certain preferred embodiments and an Example, it will be understood by those skilled in the art that the present invention extends beyond the specifically disclosed embodiments to other alternative embodiments and/or uses of the invention and obvious modifications thereof. It will be appreciated, however, that no matter how detailed the foregoing may appear in text, the invention may be practiced in many ways. Thus, it is intended that the scope of the present invention herein disclosed should not be limited by the particular disclosed embodiments described above, but should be determined only by a fair reading of the claims that follow and any equivalents thereof.

We claim:

1. A method of introducing an ultraviolet light activated viral vector into a patient's spinal tissue comprising:
   locating a light probe proximate to a spinal target cell, wherein the spinal target cell is selected from the group consisting of a chondrocyte cell and a mesenchymal cell;
   activating transduction of an ultraviolet light activated viral vector by locally administering ultraviolet light to the spinal target cell using the light probe, wherein said ultraviolet light is UVA light, wherein an intensity of UVA light is used that is equal to or greater than 500 $J/m^2$ and equal to or less than 10,000 $J/m^2$, and wherein the ultraviolet light activated viral vector comprises an adeno-associated viral vector; and
   delivering the ultraviolet light activated viral vector proximate to the spinal target cell.

2. The method according to claim 1, wherein transmitting the light occurs before delivering the vector.

3. The method according to claim 1, wherein transmitting the light occurs after delivering the vector.

4. The method according to claim 1, wherein delivering the ultraviolet light activated viral vector proximate to target cells comprises infecting the target cells with the ultraviolet light activated viral vector.

5. The method according to claim 1, wherein the light probe delivers ultraviolet light having a wavelength of about 325 nm.

6. The method according to claim 1, wherein the light probe delivers light having a wavelength from about 320 nm to about 400 nm.

7. The method according to claim 1, wherein the light probe delivers light that consists of light having a wavelength from about 320 nm to about 400 nm.

8. The method according to claim 7, wherein the light probe delivers light having a wavelength of about 322, 325, 327, 332, 337, 342, 347, 352, 357, 362, 367, 372, 377, 382, 387, 392, 393, 394, 395, 396, 397, 398, or 399 nm.

9. The method according to claim 1, wherein the light probe delivers light that consists essentially of a wavelength of about 325 nm.

10. The method according to claim 1, wherein the light probe delivers light comprising a wavelength of about 325 nm.

11. The method according to claim 1, wherein the viral vector is a recombinant adeno-associated virus (r-AAV).

12. The method according to claim 6, wherein the light probe is a laser probe and the transduction of the viral vector is activated by locally administering to the target cells ultraviolet radiation generated by the laser probe.

13. The method according to claim 6, further comprising:
removing a patient's tissue from the patient's body; and
returning the tissue to the patient's body.

14. The method according to claim 6, further comprising:
exposing the patient's tissue to the ultraviolet light without first removing the tissue from the patient's body.

15. The method according to claim 6, wherein activating the transduction of the viral vector incites bone fusion at a target site.

16. The method according to claim 6, wherein activating the transduction of the viral vector incites bone repair at a target site.

17. The method according to claim 6, further comprising;
cutting a minimal incision in the tissue blocking surgical access to a target cells; and
employing guidance tools to allow indirect visualization of the target cells.

18. A method of introducing an ultraviolet light activated viral vector into a patient's spinal tissue comprising:
inserting an implant proximate to a spinal target cell within the patient's spinal tissue, wherein the spinal target cell is selected from the group consisting of a chondrocyte cell and a mesenchymal cell;
locating a light probe proximate to the spinal target cell; and
activating the transduction of an ultraviolet light activated viral vector by locally administering ultraviolet light to the spinal target cell using the light probe, wherein the ultraviolet light activated viral vector comprises an adeno-associated viral vector, wherein said ultraviolet light comprises UVA type ultraviolet light, and wherein the UVA light is administered at an intensity of greater than or equal to 500 $J/m^2$ and less than or equal to 10,000 $J/m^2$; and
delivering the ultraviolet light activated viral vector proximate to the spinal target cells.

19. The method according to claim 18, wherein the light probe delivers ultraviolet radiation having a wavelength from 320 nm to 400 nm.

20. The method according to claim 19, wherein the light probe delivers ultraviolet radiation having a wavelength of no more than about 355 nm.

21. The method according to claim 20, wherein the light probe delivers ultraviolet radiation having a wavelength of about 325 nm.

22. The method according to claim 18, wherein the transduction of the viral vector is activated by locally administering to the spinal target cells ultraviolet light generated by a laser probe.

23. The method according to claim 18, wherein the ultraviolet light activated viral vector is a recombinant adeno-associated virus (r-AAV).

24. The method according to claim 23, wherein the light probe delivers ultraviolet light having a wavelength consisting of from about 320 nm to about 400 nm.

25. The method according to claim 24, further comprising integrating recombinant adeno-associated virus (r-AAV) with the implant prior to insertion proximate to spinal target cells.

26. The method according to claim 25, wherein integrating the recombinant adeno-associated virus (r-AAV) with the implant comprises absorbing the recombinant adeno-associated virus.

27. The method according to claim 25, wherein integrating the recombinant adeno-associated virus (r-AAV) with the implant comprises bonding the recombinant adeno-associated virus to the implant.

28. The method according to claim 25, wherein integrating the recombinant adeno-associated virus (r-AAV) with the implant comprises baking the recombinant adeno-associated virus onto the implant.

29. The method according to claim 25, further comprising the insertion of the implant as a spacer between two vertebra using minimally invasive surgical techniques.

30. The method of claim 19, wherein inserting the implant comprises spacing vertebra by attaching a structural support implant to bone.

31. The method of claim 18, wherein the intensity of the UVA light is more than 1000 $J/m^2$ and less than 6000 $J/m^2$.

32. The method of claim 1, wherein the intensity of the UVA light is more than 1000 $J/m^2$ and less than 6000 $J/m^2$.

\* \* \* \* \*

UNITED STATES PATENT AND TRADEMARK OFFICE
CERTIFICATE OF CORRECTION

| | | |
|---|---|---|
| PATENT NO. | : 7,704,272 B2 | Page 1 of 1 |
| APPLICATION NO. | : 10/357273 | |
| DATED | : April 27, 2010 | |
| INVENTOR(S) | : Rubery et al. | |

It is certified that error appears in the above-identified patent and that said Letters Patent is hereby corrected as shown below:

Title Page, Item (56) on Page 2, Column 1, Line 30, under OTHER PUBLICATIONS, please change "Protien" to --Protein--.

In Column 1, Line 5, please change "RERFERENCE" to --REFERENCE--.

In Column 4, Line 47 (Approx.), please change "UW" to --UV--.

In Column 5, Line 12 (Approx.), please change "cells," to --cells.--.

In Column 8, Line 15, please change "osico" to --osteo--.

In Column 9, Line 23, please change "6,000" to --6000--.

In Column 9, Line 33, please change "P-galactosidase" to --β-galactosidase--.

In Column 10, Line 37, in Claim 2 please change "1,wherein" to --1, wherein--.

Signed and Sealed this

Fifth Day of October, 2010

David J. Kappos
*Director of the United States Patent and Trademark Office*